United States Patent [19]

Speranza et al.

[11] Patent Number: 5,019,653

[45] Date of Patent: May 28, 1991

[54] PURIFICATION OF POLYAMINES DERIVED FROM POLYHYDROXYL COMPOUNDS

[75] Inventors: George P. Speranza, Austin; Donald H. Champion, Pflugerville, both of Tex.

[73] Assignee: Texaco Chemical Company, White Plains, N.Y.

[21] Appl. No.: 522,942

[22] Filed: May 14, 1990

[51] Int. Cl.$^5$ ............................................. C07C 209/00
[52] U.S. Cl. ................................. 564/497; 564/479; 564/491; 564/498; 564/505
[58] Field of Search .............. 564/497, 498, 505, 479, 564/491

[56] References Cited

U.S. PATENT DOCUMENTS

| | | | |
|---|---|---|---|
| 3,580,952 | 5/1971 | Moschel et al. | 564/497 |
| 3,755,447 | 8/1973 | Klemann et al. | 564/498 |
| 4,324,917 | 4/1982 | McConnell | 564/497 |
| 4,532,354 | 7/1985 | Cornils et al. | 564/497 |
| 4,731,165 | 3/1988 | Niebruegge et al. | 564/498 |
| 4,737,243 | 4/1988 | Siml et al. | 564/498 |

FOREIGN PATENT DOCUMENTS 165426  10/1982  Japan ................................. 564/497

Primary Examiner—Glennon H. Hollrah
Assistant Examiner—Scott C. Rand
Attorney, Agent, or Firm—Jack H. Park; Kenneth R. Priem; Cynthia L. Kendrick

[57] ABSTRACT

Disclosed is a method for purification of polyamines which comprises contacting said polyamines with a treating agent selected from the group consisting of oxides, hydroxides or alkoxides of elements from the group consisting of silicon or Group IIA, IIIA, IIB, IIIB, IVB or VB at a temperature of about 150° C. to 250° C. and a pressure of subatomspheric to 10 atmospheres for a period of time sufficient to lower the hydroxyl impurity level of said amines.

20 Claims, No Drawings

PURIFICATION OF POLYAMINES DERIVED FROM POLYHYDROXYL COMPOUNDS

BACKGROUND OF THE INVENTION

1. Field Of The Invention

This invention relates to the purification of polyamines and more particularly to a method for the purification of polyamines prepared by reductive amination of a polyhydroxyl compound over a suitable metal catalyst or by cyanoethylation of a polyhydroxyl compound followed by reduction of the cyanoethyl derivative which in either case contain residual hydroxyl material. The purification is accomplished by using as treating agents oxides, hydroxides or alkoxides of silicon or elements of Group IIA, IIIA, IIB, IIIB, IVB or VB (CAS) of the Periodic Table.

Typically the purity of the product can be increased more than one percent by significantly reducing the hydroxyl content. An increase of this magnitude in the purity of the product translates into very substantial advantage in a commercial situation. In addition, products made with the higher purity polyamines yield polyamides which are lighter in color.

2. Related Art

Polyoxyalkyleneamines are conventionally prepared by the reductive amination of a polyhydroxyl compound or by cyanoethylation of a polyhydroxyl compound followed by reduction of the cyanoethyl derivative. The amination generally takes place over a transition metal catalyst.

In each process a significant quantity of residual hydroxyl-containing material remains in the product, the contamination normally being at a level greater than about 100 parts per million based on the amination product.

No art has been found relating to methods of reducing the hydroxyl-containing material in the product.

SUMMARY OF THE INVENTION

This invention is directed to a method for the purification of polyoxyalkyleneamines containing greater than about 100 parts per million residual hydroxyl-containing material by treating said polyamines with an oxide, hydroxide or alkoxide of silicon or Group IIA, IIIA, IIB, IIIB, IVB or VB of the Periodic Table. Polyethylene glycol diamines may be purified, for example, with silica-alumina, alumina, aluminum isopropoxide, strontium ethoxide, titanium isopropoxide or tetraalkyl orthosilicates.

It has been discovered in accordance with the instant invention that if the polyoxyalkyleneamine is treated with about 1 to 20 wt% of one of the oxide, hydroxide or alkoxide compounds under treating conditions, including a temperature of from 150° C. to about 250° C. at subatmospheric pressure to about 10 atmospheres, for a period of time sufficient to lower the impurity level of hydroxyl material in the feedstock, the product can be subsequently filtered and/or distilled and will result in polyoxyalkyleneamines of greater than 99.5% purity. It has also been demonstrated that when these higher purity polyamines are used in making polyamides, they result in polyamides which are much lighter in color than those obtained by using the polyamines which have not undergone such a purification process.

DESCRIPTION OF THE PREFERRED EMBODIMENT

The starting materials for the present invention are polyoxyalkyleneamines having a molecular weight in the range of 100 to 2000, particularly polyoxyethylene diamines having a molecular weight in the range of 100 to 500 which are contaminated with more than about 100 parts per million, and more typically from 100 to about 10,000 parts per million of hydroxyl-containing materials. Hydroxyl materials remain after preparation by amination or cyanoethylation due to incomplete reaction of the hydroxyl groups or cleavage of an ether to produce at least one hydroxyl group which may be incompletely converted in the amination or cyanoethylation reactions.

The approximate hydroxyl content of the materials can be expressed in ppm by multiplying the gas chromatographic percentage by 10,000. For example:

$$0.07 \times 10,000 = 700 \text{ ppm}$$

The treating agents used in accordance with the present invention for purifying the diamines are oxides, hydroxides and alkoxides of silicon or Group IIA, IIIA, IIB, IIIB, IVB or VB of the Periodic Table. It has been surprisingly discovered in accordance with the present invention that these compounds are effective for the removal of hydroxyl material from polyoxyalkyleneamines when reacted with the polyamines for from about 10 minutes to 4 hours at a temperature of 150°–250° C. and subatmospheric pressure up to about 10 atmospheres. The preferred time period is about 15 minutes to 2 hours.

The method of the instant invention is intended to take advantage of the M-O bond strength in inorganic compounds to selectively remove the HO- groups (M = elements described above). (Organic materials such as carboxylic acids react more readily with the —NH$_2$ group). An example of how our invention works can be demonstrated by the case where the treating agent is a tetraalkylorthosilicate (M = Si).

Si(OR')$_4$ + 4HO—R—NH$_2$ → Si(ORNH$_2$)$_4$ + 4R'OH  Eq. I

The following represents a simplified representation of the scheme by which the reaction is believed to proceed:

M(OR')$_X$ +  Eq. II

HO—R—A ⇌ A—R—OM(OR')$_{x-1}$ + R'OH

A—ROM(OR')$_{x-1}$ +

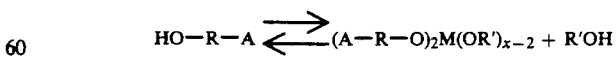

HO—R—A ⇌ (A—R—O)$_2$M(OR')$_{x-2}$ + R'OH etc.

for hydroxides (R, = H) and alkoxides (R' = alkyl), A = OH or NH$_2$.

The following diagram represents what might happen at a solid oxide surface (like silica or alumina), where if the oxide is hydrated the amino alcohol would displace water:

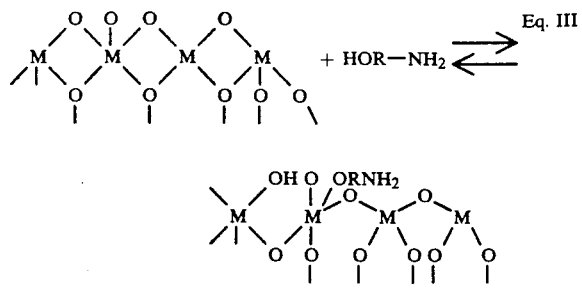

In the purification method of the instant invention the polyamines are reacted with an oxide, hydroxide or alkoxide of silicon or a Group IIA, IIIA, IIB, IIIB, IVB or VB. Suitable compounds in Group IIA contain magnesium, calcium, strontium and barium. Compounds containing these elements which are useful as treating agents in the instant invention include elemental calcium, magnesium methoxide, barium oxide and strontium ethoxide.

Suitable compounds in Group IIIA contain boron and aluminum. Treatings agents containing these elements are boric acid, aluminum isopropoxide, alumina or borate esters.

Silicon can be in a variety of forms. The silica (silicon dioxide) can also be in combination with alumina (aluminum oxide). A suitable silica-alumina treating agent which can be obtained commercially is MS 25/80, a silica-alumina compound from Davison.

Group IVB compounds contain titanium and zirconium. An example of a treating agent from this group is titanium isopropoxide.

As mentioned the polyoxyalkyleneamine is reacted with from about 1 to 20 wt%, based on the total weight of the feedstock of the treating agent. About 2 to 10 wt% is preferred.

Where the treating agent is calcium, it is beneficial if it is mixed with about 200 to 1000 wt% of polar solvent before it is brought into contact with the treating agent. Methanol was used with calcium in Example 9 to generate calcium methoxide prior to treatment of the TEGDA. Methanol is a reactive alcohol and calcium is relatively unreactive to the hydroxyl impurities.

The invention may be conducted in a batch fashion by treating a charge stock composed of a polyoxyalkyleneamine and the treating agent or it may be carried out in a continuous manner at a space velocity of about 0.5 to 4 volume of feedstock per hour, a temperature of about 150° C. to about 250° C. and a pressure of subatmospheric about 10 atmospheres for a period of time sufficient to thereby lower the level of contamination of the feedstock with hydroxyl-containing material. The contact time may vary from about 10 minutes to 4 hours.

As mentioned the reaction can be represented by:

When the alcohol formed has a boiling point below the treatment temperature, it may be distilled out during the process. The disadvantage to the reaction is that any $M(ORNH_2)_x$ or similar compound formed in the reaction which is soluble in the mixture cannot be removed by simple filtration and will require a distillation (or other separation scheme) to remove it from the treated material if the presence of such a material is undesirable.

To illustrate the process of the invention the following examples are given. It is to be understood that the examples are given in the way of illustration and are not to be regarded as limiting the invention in any way.

EXAMPLES 1–8

Purification of Triethylene Glycol Diamine

To a 250 ml three necked flask fitted with a thermometer, nitrogen bubbler and magnetic stirrer was charged 100 g impure triethylene glycol diamine and 2.0 g TYZOR ® TPT tetraisopropyl titanate. The mixture was heated to 200° C. for 1.5 hours and filtered. Gas chromatographic analysis of the filtrate showed the product contained 99.62% triethylene glycol diamine (TEGDA) and no diethylene glycol monoamine (DEGMA).

The procedure was repeated several times using different agents to treat the TEGDA (100 g), all treatments being conducted at 200° C. for 1.5 hours. Table I summarizes the results obtained.

TABLE I

Purification Of Triethylene Glycol Diamine

| Example | Treating Agent | Mass | GC % TEGDA | ppm DEGMA |
|---|---|---|---|---|
| | — | | 99.56 | 700 |
| 1 | titanium isopropoxide | 2.0 g | 99.62 | nil |
| 2 | strontium ethoxide | 1.0 | 99.85 | nil |
| 3 | sodium methoxide | 0.5 | 75.86 | 172,400 |
| 4 | magnesium methoxide | 1.0 | 99.81 | nil |
| 5 | boric acid | 2.0 | 99.90 | nil |
| 6 | aluminum isopropoxide | 1.0 | 99.89 | nil |
| 7 | basic alumina | 2.0 | 99.81 | nil |
| 8 | silica-alumina (Davison MS 25/80) | 4.0 | 99.65 | nil |

EXAMPLE 9

To a 250 ml three necked flask fitted with a thermometer, nitrogen bubbler and magnetic stirrer was charged 0.5 g calcium and 10 ml methanol. After stirring for 40 minutes at 70° C., 100 g impure TEGDA was added and the mixture was heated to 200° C. for 1.5 hours as lights were removed by use of a Dean-Stark trap. The resulting mixture in the pot was filtered. Gas chromatographic analysis of the filtrate showed the product to consist of 99.75% TEGDA with no DEGMA being detected.

EXAMPLE 10

A 500 g sample of TEGDA (99.25%, containing 0.50% DEGMA) was treated with 15 g of boric acid as in Example 1. The mixture was then filtered and distilled. The middle cut (337 g, bp. 129–132 C/20 mm Hg) was found to contain 99.60% TEGDA and 0.29% DEGMA according to GC analysis.

EXAMPLES 11–15

Purification Of Tetraethylene Glycol Diamine (T4EGDA)

Tetraethylene glycol diamine (100 g) was treated as in Example 1 with various agents. The products were analyzed by gas chromatography to give the results listed in Table II.

TABLE II

Purification Of Tetraethylene Glycol Diamine

| Example | Treating Agent | Mass | GC % T4EGDA | ppm DEG | ppm TEGMA | ppm T4EG | ppm Total Hydroxyl Impurities |
|---|---|---|---|---|---|---|---|
| — | (untreated sample) | — | 99.47 | 370 | 1560 | 2880 | 4810 |
| 11 | silica-alumina (Davison MS 25/80) | 4.0 g | 99.50 | 220 | 1170 | 2590 | 3980 |
| 12 | boric acid | 3.0 | 99.46 | nil | nil | 3340 | 3340 |
| 13 | strontium ethoxide | 2.0 | 99.18 | nil | nil | 4480 | 4480 |
| 14 | magnesium methoxide | 2.0 | 99.40 | nil | nil | 4470 | 4470 |
| 15 | basic alumina | 4.0 | 99.15 | nil | nil | 4740 | 4740 |

DEG = diethylene glycol, TEGMA = triethylene glycol monoamine, T4EG = tetraethylene glycol The rate of reaction with T4EGDA is harder to interpret because the T4EG content goes up.

EXAMPLE 16

A 500 g sample of diethylene glycol diamine (DEGDA) which was 98.71% pure was treated with 20 g of boric acid as in Example 1. The mixture was then filtered and distilled. The middle cut (316 g, bp. 185° C.) was found to contain 99.29% DEGDA by GC analysis. The next cut collected (63 g) was found to contain 99.32% DEGDA.

To a side arm test tube immersed in an oil bath and equipped with a purified nitrogen flow was charged an 18×150 mm test tube containing a mixture of 1.46 g adipic acid, 1.04 g unpurified DEGDA and 1.0 g water. After heating at 250° C. for 3 hours, a dark yellow polyamide was obtained. Substituting the distilled materials obtained from the above procedure for the impure DEGDA provided polyamides which were much lighter than those obtained by using the impure DEGDA.

EXAMPLE 17

A 250 g sample of impure 4,9-dioxadodecane-1,12-diamine was treated with 8 g of boric acid as in Example 1. The mixture was then filtered and distilled to give 165 g distillate (bp. 152/2.1-117 C/0.8 mm Hg) and 60 g bottoms.

The test tube apparatus described in Example 16 was charged with a mixture of 1.46 g adipic acid, 2.04 g unpurified 4,9-dioxadodecane-1,12-diamine and 1.0 g water. Upon heating to 230° C. a yellow color developed in the reaction mixture. The color darkened considerably after 3 hours of heating.

Following the same procedure, the treated and distilled diamine did not cause color after heating 3 hours at 240° C.

What is claimed is:

1. A method for the purification of polyamines which comprises contacting said polyamines with a treating agent selected from the group consisting of oxides, hydroxides or alkoxides of elements from the group consisting of silicon or Group IIA, IIIA, IIB, IIIB, IVB or VB (CAS designation) of the Periodic Table at a temperature of about 150° C. to 250° C. and a pressure of subatmospheric to 10 atmospheres for a period of time sufficient to lower the impurity level of said materials in the amines.

2. The method of claim 1 wherein the polyamine is a polyoxyalkylene amine.

3. The method of claim 1 wherein the polyamine is a polyethylene glycol diamine.

4. The method of claim 3 wherein the polyethylene glycol diamine is selected from the group consisting of diethylene glycol diamine, triethylene glycol diamine and tetraethylene glycol diamine.

5. The method of claim 1 wherein the treating agent is selected from the group consisting of an oxide, hydroxide or alkoxide of an element of Group IIA of the Periodic Table.

6. The method of claim 1 wherein the treating agent is selected from the group consisting of an oxide, hydroxide or alkoxide of an element of Group IIIA of the Periodic Table.

7. The method of claim 1 wherein the treating agent is selected from the group consisting of an oxide, hydroxide or alkoxide of an element of Group IIB of the Periodic Table.

8. The method of claim 1 wherein the treating agent is selected from the group consisting of an oxide, hydroxide or alkoxide of an element of Group IIIB of the Periodic Table.

9. The method of claim 1 wherein the treating agent is selected from the group consisting of an oxide, hydroxide or alkoxide of an element of Group IVB of the Periodic Table.

10. The method of claim 1 wherein the treating agent is selected from the group consisting of an oxide, hydroxide or alkoxide of an element of Group VB of the Periodic Table.

11. The method of claim 1 wherein the treating agent is selected from the group consisting of a silicon oxide, hydroxide or alkoxide.

12. The method of claim 5 wherein the treating agent is selected from the group consisting of magnesium methoxide and strontium ethoxide.

13. The method of claim 6 wherein the treating agent is selected from the group consisting of boric acid, aluminum isopropoxide and aluminum oxide (alumina).

14. The method of claim 1 wherein the treating agent is silica-alumina.

15. The method of claim 9 wherein the treating agent is titanium isopropoxide.

16. The method of claim 1 wherein the temperature is from about 150° C. to 250° C.

17. The method of claim 1 wherein the pressure is from subatmospheric to about 10 atmospheres.

18. A method for purification of polyoxyalkyleneamines containing residual hydroxyl-containing material which comprises contacting said polyoxyalkylene amines with a treating agent selected from the group consisting of magnesium methoxide, strontium ethoxide, boric acid, aluminum isopropoxide, alumina, silica-alumina or titanium isopropoxide for a period of time sufficient to lower the impurity level of said hydroxyl groups in the amines.

19. The method of claim 18 wherein the polyoxyalkyleneamines are polyoxyethyleneamines.

20. The method of claim 19 wherein the polyoxyethylenediamines are selected from the group consisting of diethylene glycol diamine, triethylene glycol diamine and tetraethylene glycol diamine.

* * * * *